United States Patent [19]
Barger et al.

[11] Patent Number: 5,620,894
[45] Date of Patent: Apr. 15, 1997

[54] APPARATUS FOR AUTOMATED BIOLOGICAL CELL HARVESTING

[75] Inventors: Lee A. Barger, Cary; Brisco L. Harward, Apex; Douglas K. Hoeppner, Raleigh, all of N.C.

[73] Assignee: Glaxo Wellcome Inc., Research Triangle Park, N.C.

[21] Appl. No.: 491,417

[22] Filed: Jun. 16, 1995

[51] Int. Cl.$^6$ .............................. C12M 1/12; B01D 29/00
[52] U.S. Cl. ...................... 435/286.2; 435/286.4; 435/308.1; 422/101; 210/232; 210/405; 210/406; 210/416.1
[58] Field of Search .................. 435/286.1, 286.2, 435/286.4, 286.5, 287.3, 288.3, 288.4, 297.5, 305.1, 305.2, 308.1; 422/63, 65, 100, 101, 102; 210/405, 406, 416.1, 323, 258

[56] References Cited

U.S. PATENT DOCUMENTS

| | | | |
|---|---|---|---|
| 4,245,042 | 1/1981 | Weinstein et al. | 435/30 |
| 4,304,865 | 12/1981 | O'Brien et al. | 435/240 |
| 4,496,657 | 1/1985 | Coppersmith et al. | 435/287 |
| 4,783,877 | 11/1988 | Vince | 15/302 |
| 4,952,518 | 8/1990 | Johnson et al. | 422/65 |
| 4,988,482 | 1/1991 | Weston | 422/100 |
| 5,190,666 | 3/1993 | Bisconte | 435/308.1 |
| 5,244,630 | 9/1993 | Khalil et al. | 422/101 |
| 5,273,718 | 12/1993 | Skold et al. | 422/100 |
| 5,380,437 | 1/1995 | Bertoncini | 210/406 |
| 5,432,085 | 7/1995 | Warren et al. | 422/100 |

FOREIGN PATENT DOCUMENTS

| | | |
|---|---|---|
| 0080134 | 6/1986 | European Pat. Off. . |
| 2225223 A | 5/1990 | United Kingdom . |
| WO87/01616 | 3/1987 | WIPO . |

*Primary Examiner*—William H. Beisner
*Attorney, Agent, or Firm*—Richard E. Jenkins; Charles E. Dadswell

[57] ABSTRACT

An automated biological cell harvesting apparatus including a fluid dispensing head adapted to move to a lowered position and dispense fluid from a plurality of spray ports, a fixed upper tray positioned beneath the fluid dispensing head for supporting a biological filter plate of the type defining a plurality of fluid permeable wells therein, a vertically movable lower tray adapted to move from a lowermost position to a raised position in engagement with the upper tray. A controller is provided for dispensing fluid from the fluid dispensing head into the wells of the filter plate, and raising the lower tray into its raised position in engagement with the upper tray and then creating a vacuum between the lower tray and the upper tray to draw the fluid from the filter plate supported on the upper tray into the lower tray for collection in a microplate with a corresponding number of wells or, in the absence of a microplate, for removal of the fluid from the lower tray to a remote common waste collection vessel.

21 Claims, 8 Drawing Sheets

5,620,894

APPARATUS FOR AUTOMATED BIOLOGICAL CELL HARVESTING

TECHNICAL FIELD

The present invention relates to an apparatus for biological cell harvesting, and more particularly to an automated apparatus for harvesting biological cells from fluid carried within biological filter plates.

BACKGROUND ART

Laboratory scientists are familiar with the multi-step, semi-manual methods for biological cell harvesting from biological filter plates and the tedious and laborious effort involved in so doing. Recognizing the need for an automated biological cell harvesting apparatus to facilitate this procedure, applicants have developed the novel apparatus described hereinafter.

Very significantly, applicants discovered that an existing microplate washer, Model No. SLT 96PW available from Tecan USA, Inc. of Research Triangle Park, N.C., could be modified to achieve an entirely unintended function as an automated cell harvesting apparatus.

As known to those skilled in the art, the SLT 96PW microplate washer is a programmable microplate washer which utilizes an internal microprocessor control to wash/aspirate 96 well microplates. The MILLIPORE brand 96 well microplate is a well known brand of microplate, although other pharmaceutical support companies also distribute 96 well microplates.

In its original form, the SLT 96PW microplate washer apparatus comprises a fluid pump connected to a fluid dispensing head, a vacuum switch to initiate aspiration, a fixed tray for receiving a microplate to be washed, and a microcontroller for controlling the fluid dispensing and aspirating sequence achieved by 96 pairs of dispense/aspirate tubes provided in the dispensing head.

The microcontroller of the SLT 96PW microplate washer provides flexibility to the apparatus by allowing for programmable variations in the soak and aspirate times as well as in the volume and speed of fluid dispensing. The wash process in the SLT 96PW includes the following programmable parameters: the amount of fluid to dispense; the soak time; the aspirate time; and the number of times the cycle should be repeated for a microplate. As an option, the SLT 96PW includes a RS232 serial interface port that allows the apparatus to communicate synchronously with a personal computer or robot. In this mode, commands can be issued to the apparatus that specify the wash program to run, and the SLT 96PW can send response signals to these commands with a variety of codes indicating the status of the apparatus.

The fluid dispensing head of the SLT 96PW rides on a vertical track and has 96 pairs of stainless steel tubes depending downwardly from the bottom surface thereof. Each pair of stainless steel tubes includes a relatively shorter tube to dispense fluid and a relatively longer tube to aspirate the well in which the pair of tubes is positioned. The vertical track and a precision electric stepper motor allow the fluid dispensing head to be optimally vertically positioned for introducing/removing microplates and dispensing and removing fluid from the microplates. The 96 pairs of stainless steel tubes depending from the fluid dispensing head correspond to each of the 96 wells in sample microplates. Within each pair of stainless steel tubes, as noted hereinabove, one tube is used exclusively to dispense fluid from a common manifold, and the other tube is used exclusively to remove the fluid from the well by suction (aspiration). Once the fluid is removed from the 96 wells of the microplate, it is collected as waste in a remote container.

The SLT 96PW uses a double-diaphragm electric pump driven by a stepper motor with an optical shaft encoder for delivery of fluid. In the dispense mode, the pump can deliver between 25 and 300 microliters (ml) of liquid in 25 microliter (ml) increments. In the wash mode, the fluid pump can be programmed to deliver between 50 and 3000 microliters (ml) of liquid in 50 microliter (ml) increments, and the rate at which the fluid is dispensed can also be programmed into the apparatus.

The SLT 96PW has a manual, horizontally slidable tray for positioning microplates beneath the fluid dispensing head and a conventional LCD display to facilitate manual operation of the apparatus.

As would be appreciated by one skilled in the art of biological cell harvesting, the SLT 96PW as provided by the manufacturer was not intended for use as a cell harvester and cannot do so due to certain inherent features. For example, the fluid dispensing head has a tendency to remove biological cells intended for harvesting when fluid is removed from the wells of a filter plate placed therein. Also, the apparatus does not have any capability to collect the fluid from the individual wells of a filter plate in distinct containers which is desirable in many laboratory studies.

The stainless steel fluid dispensing tubes direct the flow of liquid directly down into the wells of a filter plate in such a manner that the fluid streams have a tendency to stir up biological cells that may have settled at the bottom of the wells. Also, in order for the original SLT 96PW to aspirate or remove liquid from the wells of a filter plate, the relatively long aspiration tubes must be immersed in the fluid. This dipping of the aspiration tubes into the fluid in the wells creates an opportunity for cross-contamination and, even more significantly, since there is no mechanism to separate the cells from the liquid, the cells themselves can be removed along with the liquid.

Finally, in some studies it is beneficial to collect the fluid from each of the filter plate wells in corresponding distinct containers, and the SLT 96PW with its common aspiration manifold has no means of collecting fluid from each well in a distinct container. Thus, these and other limitations which would be well known to one skilled in the art of cell harvesting would normally not lead one to attempt to use the SLT 96PW microplate washer as an apparatus for biological cell harvesting, a tedious procedure presently requiring the use of several devices and incorporating a number of manual steps.

Therefore, applicants' apparatus for automated biological cell harvesting is believed to fill a long-felt need for an automated apparatus for biological cell harvesting which obviates the need for the multiple step, semi-manual procedure presently utilized in the art. The simple-to-use and highly reliable automated biological cell harvesting apparatus described and claimed hereinafter meets these and other long-felt needs in the art for such an apparatus.

DISCLOSURE OF THE INVENTION

In accordance with the present invention, there is provided an apparatus for automated biological cell harvesting which comprises a vertically movable fluid dispensing head adapted to move from a raised position to a lowered dispensing position and including a plurality of spray nozzles depending from the bottom surface of the head. A fixed upper tray is positioned beneath the fluid dispensing head and adapted to support a biological filter plate thereon having a plurality of fluid permeable wells therein corresponding to the plurality of dispensing head spray nozzles, and the upper tray being fluid permeable to allow fluid from the biological filter plate to flow therethrough. A vertically movable lower tray is positioned beneath the upper tray and adapted to move from a lowered position beneath the upper tray to a raised position in engagement with the upper tray.

First actuator means is provided to move the dispensing head from the raised position to the lowered position, and second actuator means is provided to move the lower tray from the lowered position to the raised position. A pump is provided to pump fluid through the fluid dispensing head when the dispensing head is in the lowered position, and vacuum means is provided to create a vacuum between the upper and lower trays when the lower tray is moved to its raised position. This vacuum draws fluid from the wells of a biological filter plate supported on the upper tray into the lower tray so as to isolate biological cells within the wells of the filter plate. Finally, controller means is provided for selectively activating the first and second actuator means, the pump means and the vacuum means according to a predetermined time sequence.

It is therefore an object of the present invention to provided an apparatus for automated biological cell harvesting to replace the multi-step, semi-manual cell harvesting procedure presently known in the art.

It is another object of the present invention to provide an apparatus for automated biological cell harvesting which is easy to use and provides highly reliable and reproducible cell harvesting results.

Some of the objects of the invention having been stated hereinabove, other objects will become evident as the description proceeds, when taken in connection with the accompanying drawings as best described hereinbelow.

BEST MODE FOR CARRYING OUT THE INVENTION

Modifications To SLT 96PW Washer

Applicants discovered that an SLT 96PW microplate washer available from Tecan USA, Inc. of Research Triangle Park, N.C. could be modified so as to perform the biological cell harvesting function in an automated fashion. This discovery is quite significant since heretofore the cell harvesting procedure is a multi-step, semi-manual procedure which leaves much to be desired. Although the detailed description relates to modification of the SLT 96PW apparatus, applicants contemplate that the novel modifications could be made to other similar apparatus or an original automated cell harvesting apparatus could be manufactured incorporating the novel features described herein.

Figure 1:
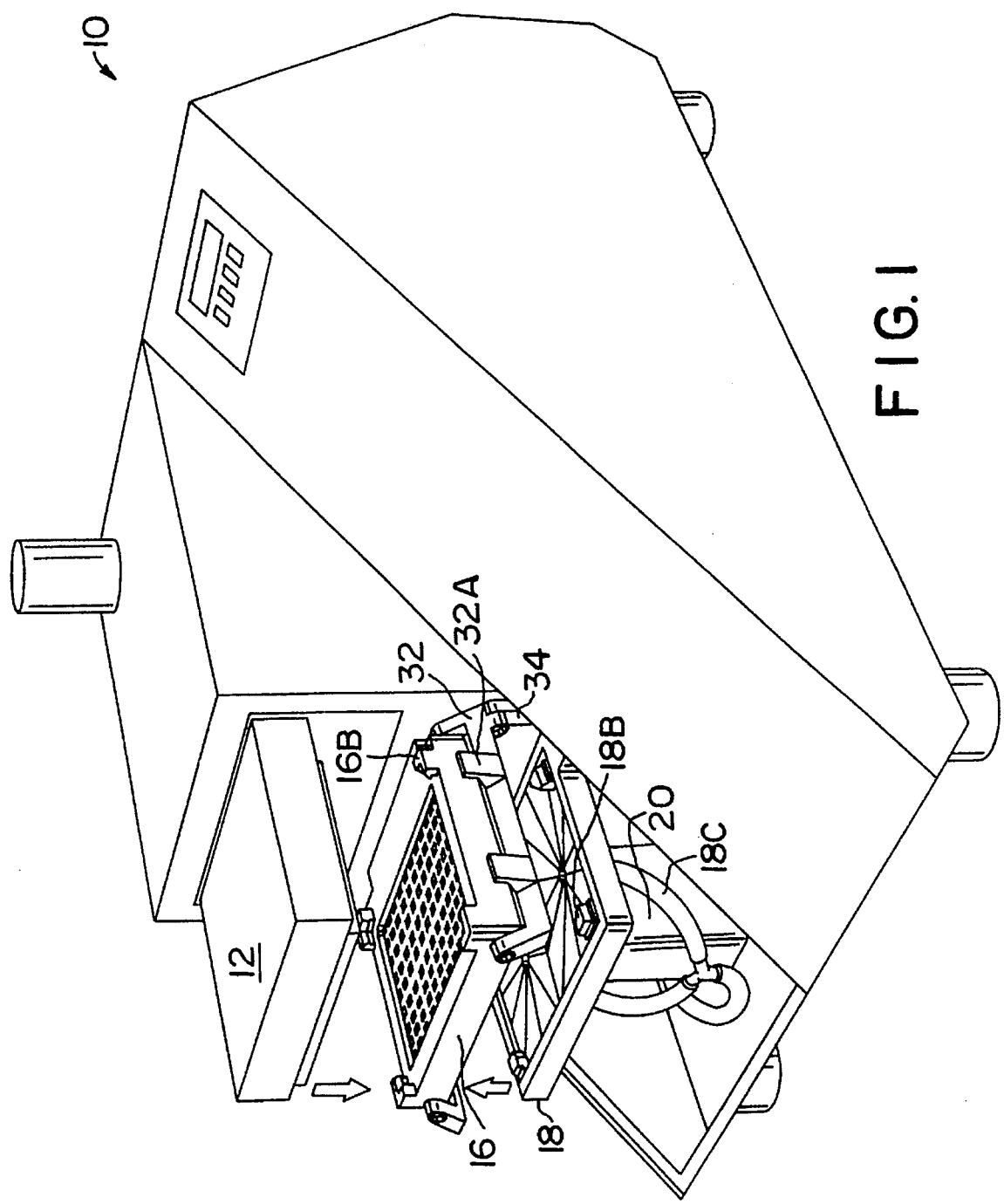
FIG. 1 is a perspective view of the apparatus for automated biological cell harvesting according to the present invention.
Figure 2:
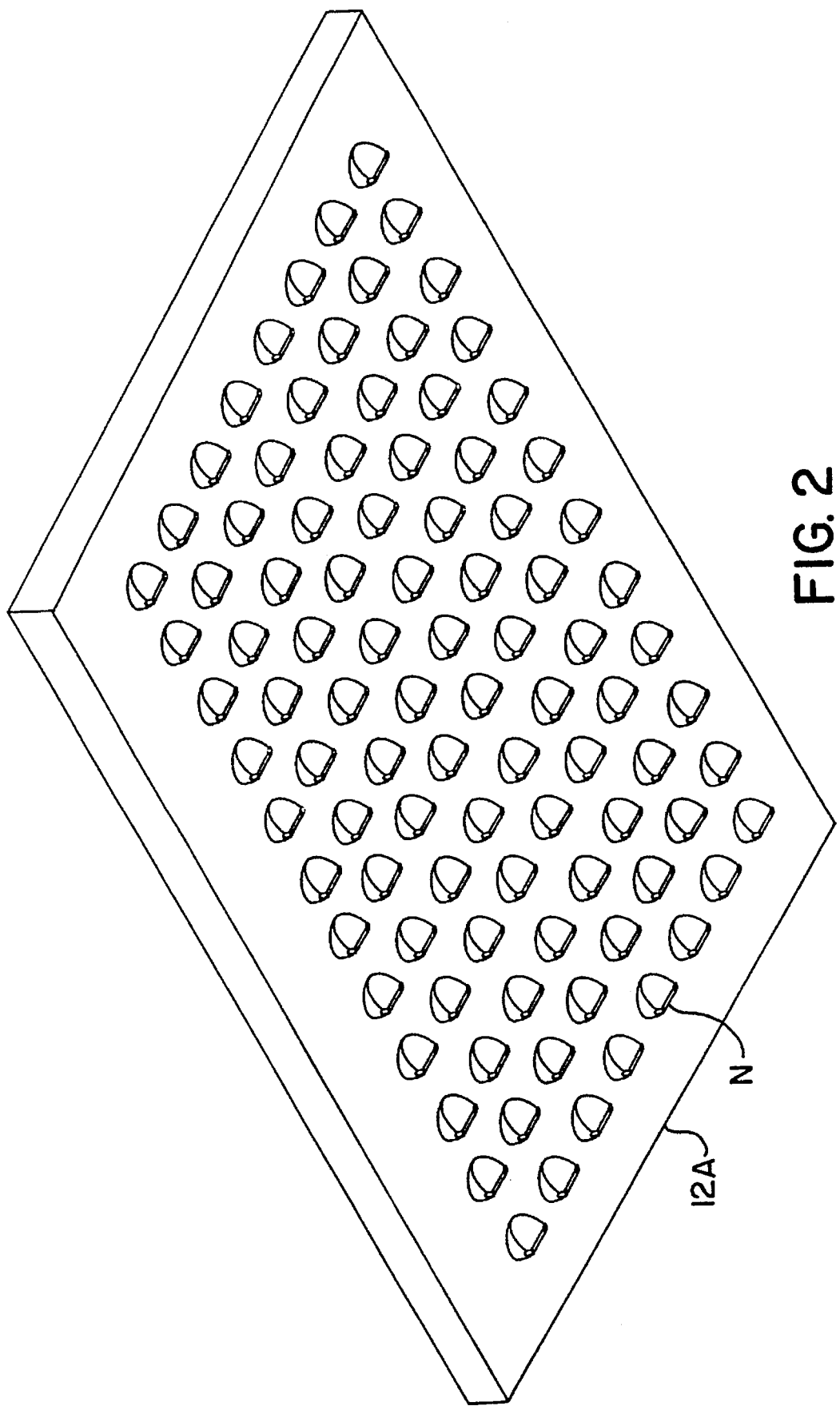
FIG. 2 is a bottom perspective view of the dispensing head of the apparatus shown in FIG. 1.

Referring now to FIGS. 1–10 of the drawings, the apparatus for automated biological cell harvesting is shown in FIG. 1 and generally designated 10. Apparatus 10 comprises a vertically movable fluid dispensing head 12 which is vertically actuated by electric motor 14. A fixed upper tray 16 for supporting a biological filter plate thereon is positioned beneath fluid dispensing head 12, and a vertically movable lower tray 18 is provided below upper tray 16 and vertically actuated by pneumatic cylinder 20, most suitably a PHD, Inc. brand, Part No. COA1C3/4×11/2-U1 pneumatic cylinder. A liquid pump 22 is fluidly connected to dispensing head 12 and provides fluid thereto upon actuation. The motherboard controller 24 acts to actuate dispensing head 12, liquid pump 22 and vacuum valve 26. Applicants have used the signal that actuates vacuum valve 26 to control 4-way solenoid valve 30, most suitably a HUMPHREY PRODUCTS brand Part No. H030-4E1 solenoid valve, via the accessory board circuit 28 (see FIG. 9). 4-way solenoid valve 30 server to actuate pneumatic cylinder 20.

Figure 9:
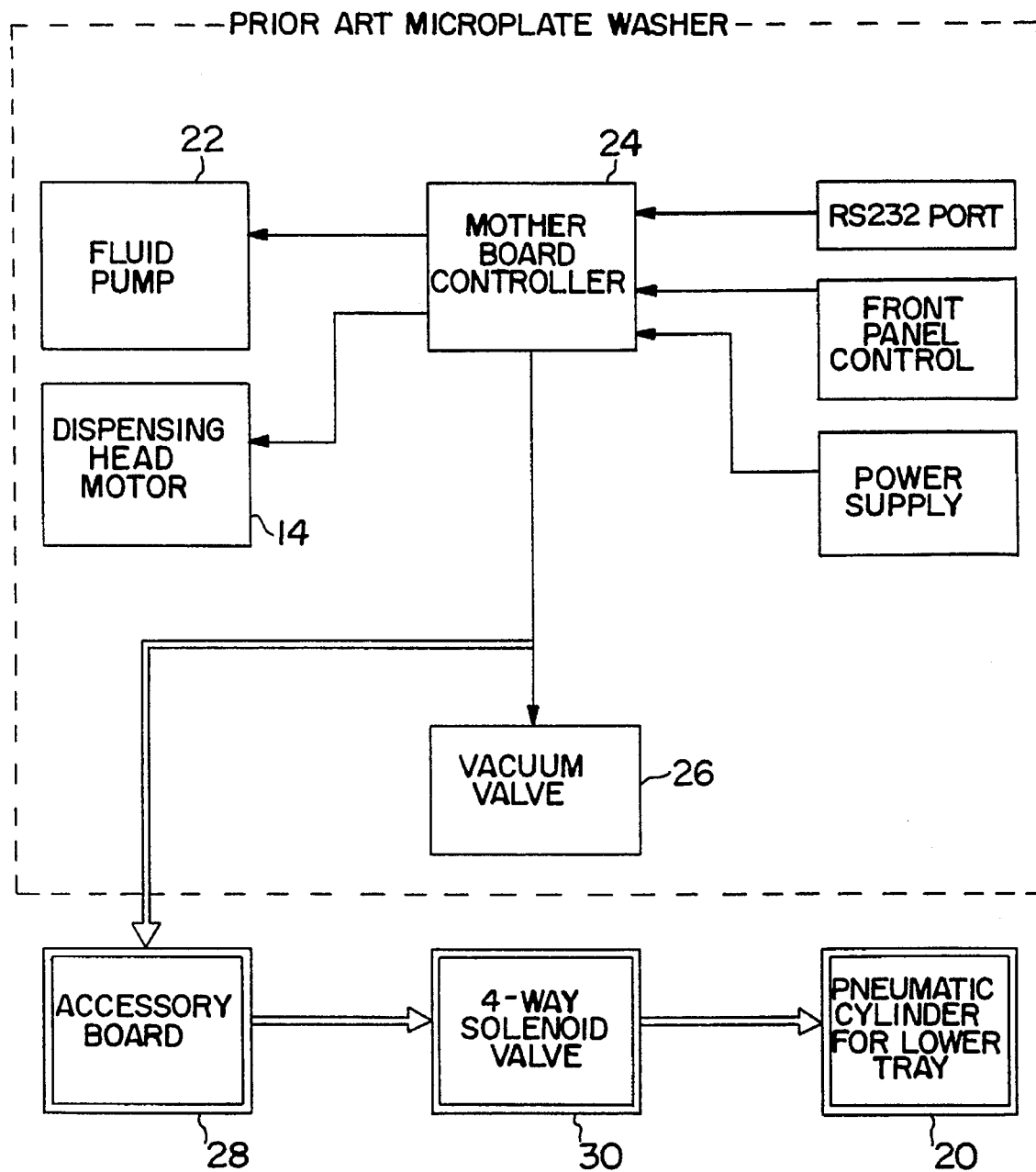
FIG. 9 is a simplified schematic of the electronic and pneumatic control mechanisms of the apparatus shown in FIG. 1.
Figure 10:
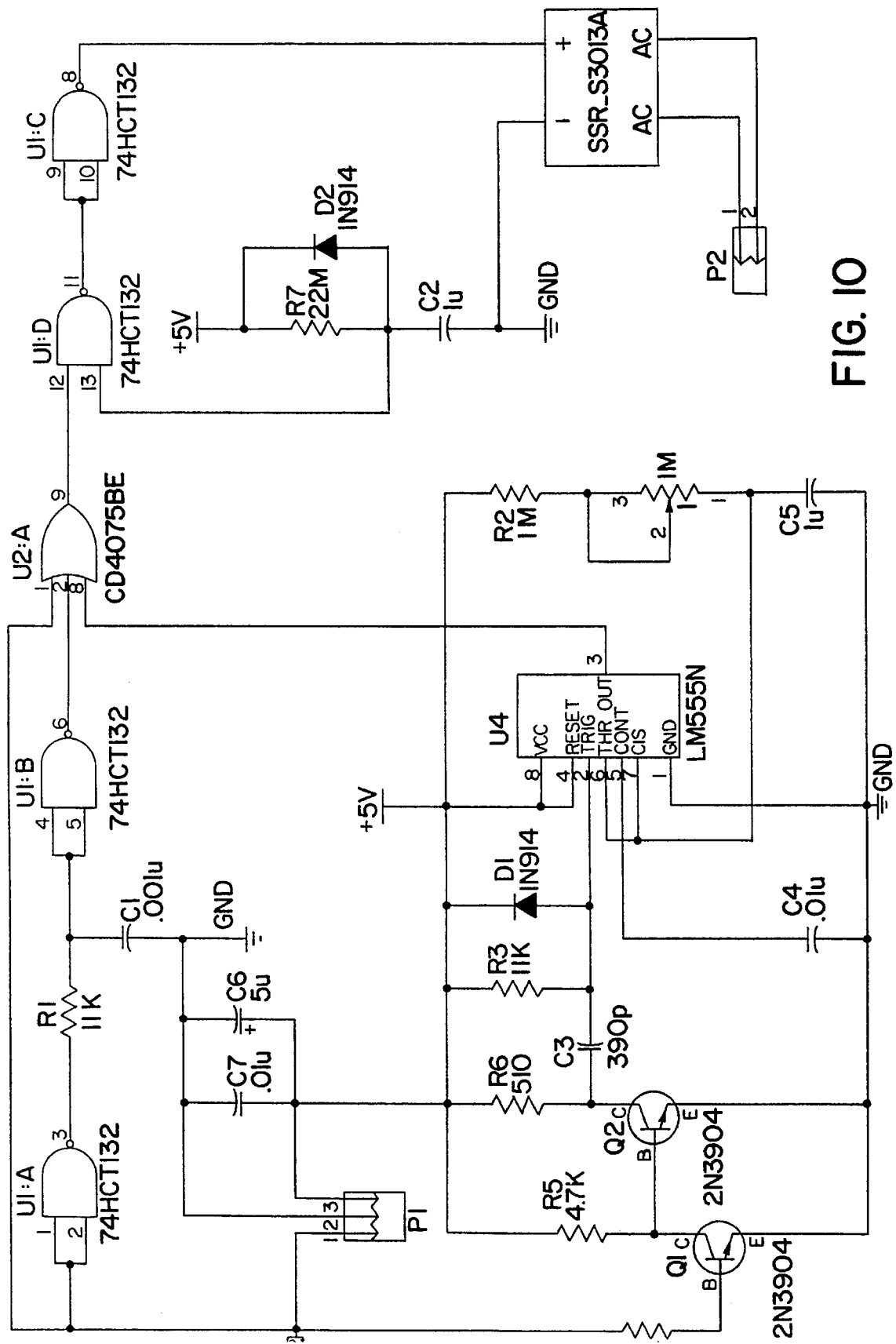
FIG. 10 is an electrical schematic of the accessory board shown in FIG. 9.

The new componentry and circuitry of applicants' apparatus can best be appreciated with reference to FIG. 9 wherein it can be seen that all of the circuitry is conventional to the SLT 96PW washer except for accessory board circuit 28, 4-way solenoid valve 30 and pneumatic cylinder 20 which are all actuated by virtue of the electrical connection of accessory board circuit 28 (see schematic in FIG. 10) to the line leading from motherboard controller 24 to vacuum valve 26. Although a specific circuit for accessory board 28 is shown in FIG. 10, applicants believe other circuits could be utilized as a matter of design choice and thus do not wish to limit the instant invention thereto.

An apparatus suitable for biological cell harvesting must be capable of dispensing a known fluid volume and removing the fluid from the 96 individual filter plate wells with minimal disturbance to the biological cells. The apparatus must also be capable of collecting the liquid from each filter plate well in a corresponding distinct container. Although applicants describe a 96 well filter plate and 96 nozzle dispensing head herein, applicants do not wish to be limited to this specific number of filter plate wells or dispensing head nozzles but use it for purposes of illustration only.

In order to prevent agitation of biological cells in the bottom of the filter plate wells, fluid dispensing head 12 must be modified so that the flow from the common manifold is not directed straight down but is angled so that it sprays against the sides of the filter plate wells. Although this can be accomplished in a number of ways, applicants utilize a machined dispensing head plate 12A (shown in FIG. 2) that provides 96 ducts, nozzles or ports (hereinafter referred to as "nozzles") which each direct fluid flow from the nozzle outwardly through 2 diverging apertures and each aperture defines a spray angle of about 45° to the surface of head plate 12A.

Figure 3:
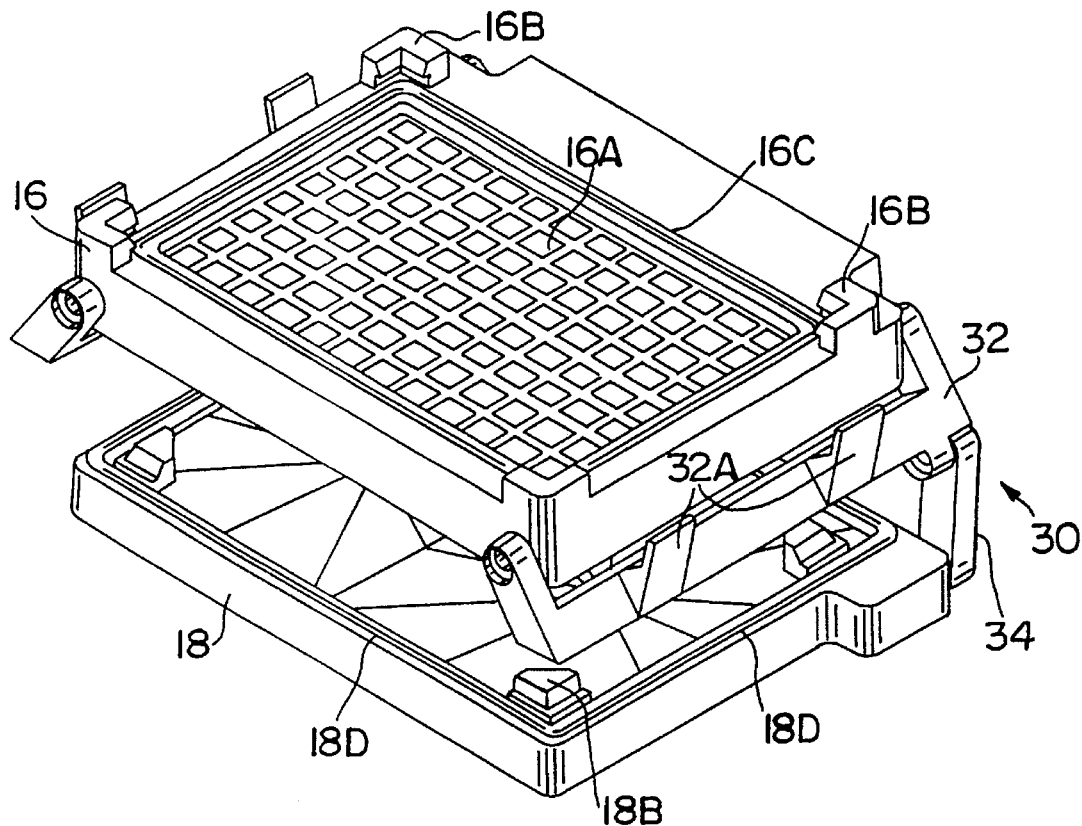
FIG. 3 is a perspective view of the upper and lower trays of the apparatus shown in FIG. 1 with the bottom tray in its lowered position.
Figure 4:
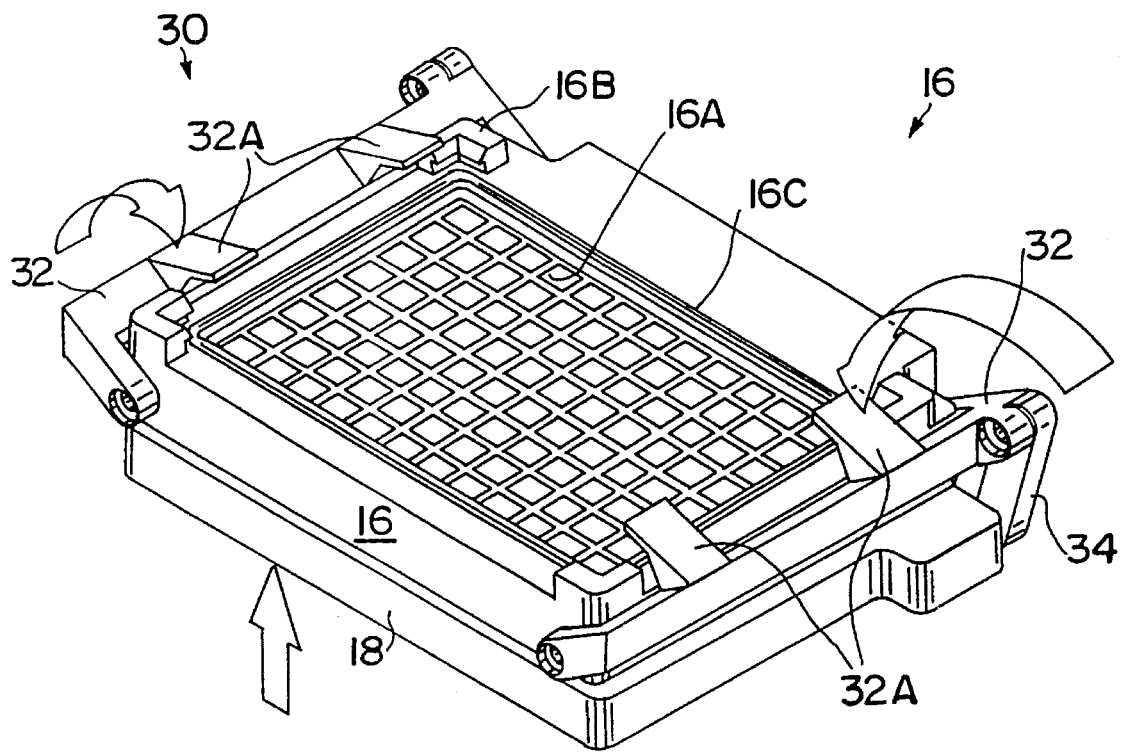
FIG. 4 is a perspective view of the upper and lower trays of the apparatus shown in FIG. 1 with the lower tray in its raised position.
Figure 3A:
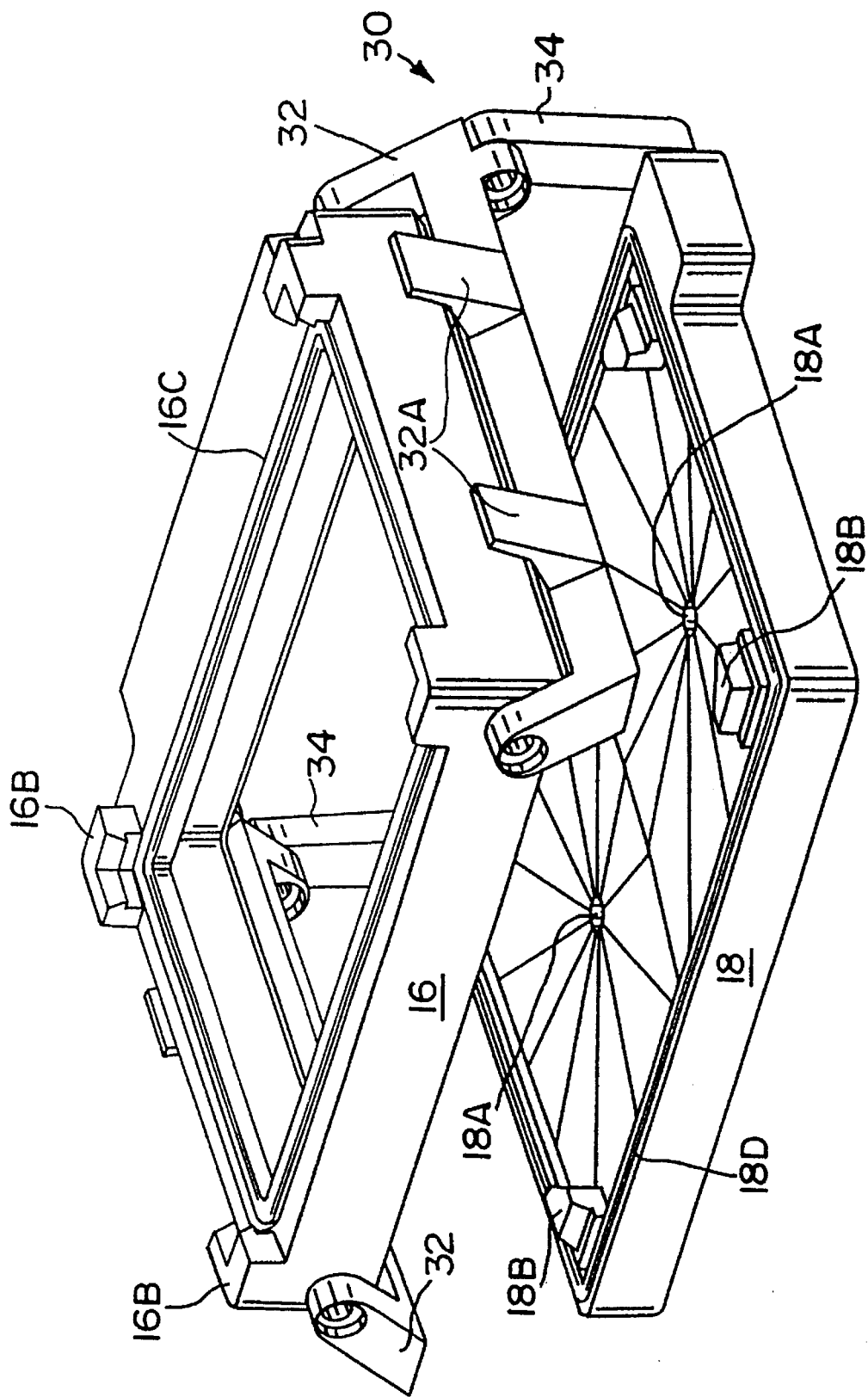
FIG. 3A is a view similar to FIG. 3 but illustrating a second embodiment of the upper tray thereof.
Figure 5:
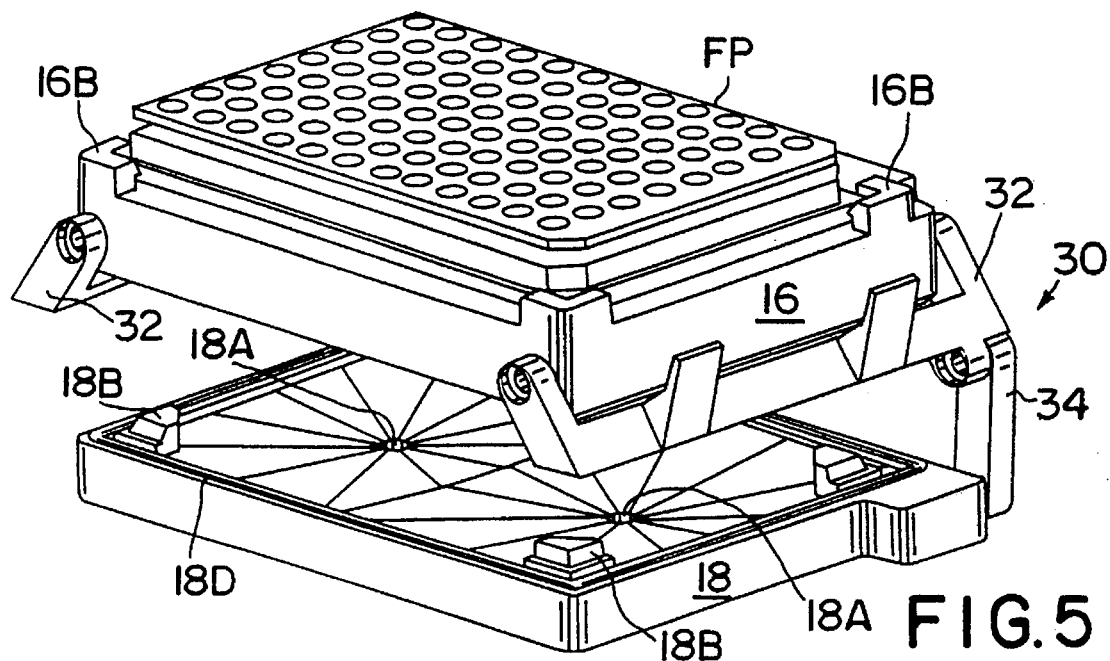
FIG. 5 is a perspective view similar to FIG. 3 but showing a biological filter plate positioned on the upper tray.
Figure 6:
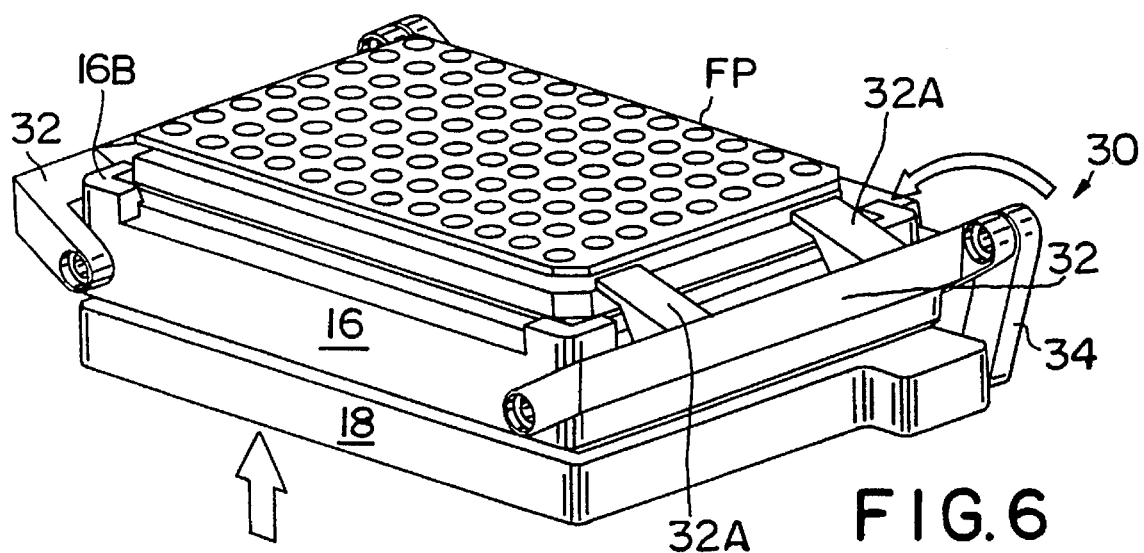
FIG. 6 is a perspective view similar to FIG. 4 but showing a biological filter plate positioned on the upper tray.
Figure 7:
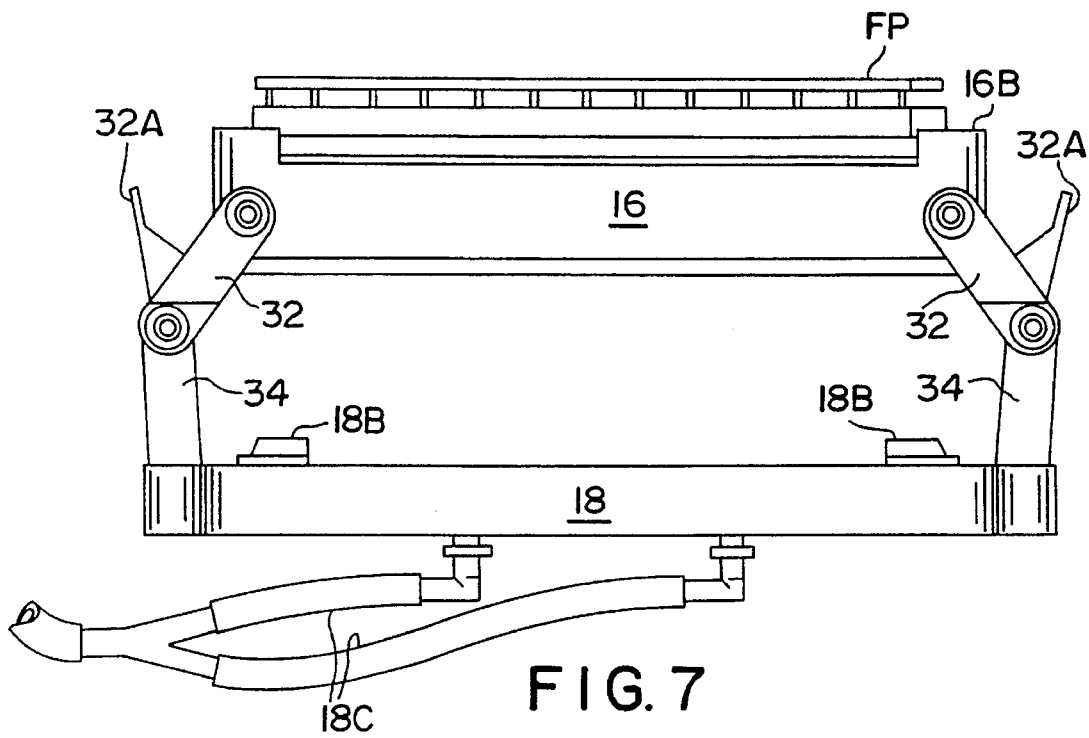
FIG. 7 is a front elevation view of the upper and lower trays shown in FIG. 5.
Figure 8:
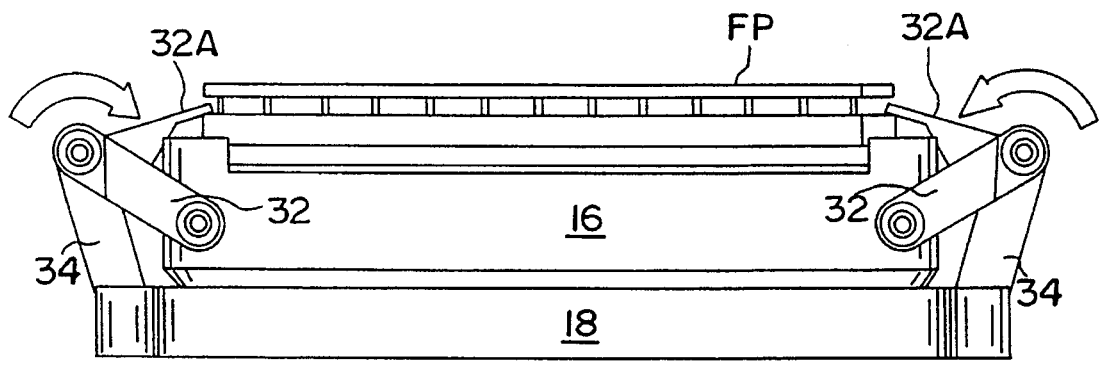
FIG. 8 is a front elevation view of the upper and lower trays shown in FIG. 6.

In order to separate the liquid from the biological cells in 96 well filter plate FP, the prior art utilizes commercially available, hand-operated units wherein vacuum is applied to the bottom of the filter plates to draw the liquid through the filter in the bottom of each well so as to leave only the biological cells in the 96 wells. Applicants' apparatus 10 allows for placing filter plate FP into upper tray 16 which has a bottom surface defining 96 apertures 16A therein in vertical registration with the bottom of the 96 wells of filter plate FP. A bottom surface is most suitably provided to upper tray 16 as shown in FIG. 3 in order to support the bottom of filter plate FP during the vacuum removal of the fluid from the wells thereof as described hereinbelow. An alternative embodiment is shown in FIG. 3A wherein upper tray 16 defines a substantially open bottom when the additional support of filter plate FP may not be necessary. Upper tray 16 includes raised corners 16B to facilitate alignment of filter plates FP within upper plate 16 during use of apparatus 10.

As a matter of procedural choice, a conventional solid bottom 96 well microplate can be placed on lower tray 18 beneath filter plate FP to catch the liquid in 96 corresponding and distinct containers as it is pulled from the individual wells of filter plate FP during the vacuum step of apparatus 10. If collection of the fluid in distinct containers is not desired, a microplate is not positioned on lower tray 18 and the fluid removed from filter plate FP can flow through the two apertures 18A in the bottom of lower tray 18 into a common waste collection vessel (not shown).

For the collection of liquid in distinct containers, the bottom microplate should be positioned on lower tray 18 over self-aligning posts 18B to assure proper positioning of the fluid collection microplate. The bottom of lower tray 18 is most suitably tapered toward apertures 18A so that when collection of fluid in the individual containers of a microplate is not desired, the fluid will flow to the low points where vacuum lines 18C (see FIG. 7) are attached. Also, upper tray 16 defines a collar around the bottom surface thereof which acts to form a tight union with elastomeric seal 18D provided around the top surface of lower tray 18 when upper tray 16 and lower tray 18 are engaged and vacuum applied during the fluid removal step of apparatus 10.

A pneumatic cylinder 20 is used to raise lower tray 18, although an electric motor or other suitable mechanism can be utilized. Lower tray 18 will be used only when aspirating filter plate FP in upper tray 16 in order to harvest the cells therein. The electrical signal for raising lower tray 18 is acquired from the SLT 96PW vacuum valve 26. Accessory board circuit 28 acts to trigger the rise of bottom tray 18 when the vacuum valve initiates the vacuum. Accessory board circuit 28 also acts to lower tray 18 after the vacuum is released by solenoid vacuum valve 26. Accessory board 28 is designed to provide a short delay between releasing the vacuum and lowering tray 18 to facilitate equalization of the pressure between upper tray 16 and lower tray 18. Equalization of pressure is aided through a small hole in the wall of the upper tray 16 (not shown).

Detailed Description of Modifications To SLT 96PW Washer

Applicants provide a new nozzle manifold and nozzle plate or dispensing head plate 16A to replace the original dispensing head and stainless steel tubes of the SLT 96PW apparatus. Dispensing head plate or nozzle plate 12A has 96 nozzles N (see FIG. 2) wherein each nozzle N has two holes drilled on a 45° angle to direct the fluid flow to the sides of the filter plate wells. The two holes are supplied with fluid through a blind hole drilled through the upper side of dispensing head plate 12A, and the blind holes transport the liquid from the manifold block to all 192 ports of 96 nozzles N. Nozzles N are most suitably configured with tapered edges to minimize the amount of fluid collecting on dispensing head plate 12A, but could also be fabricated using small bore stainless steel "Y" shaped nozzles. Nozzles N allow the ports to be lowered just below the lips of the filter plate wells in order to reduce splashing within the wells.

The original sliding tray of the SLT 96PW has been replaced by fixed upper tray 16 (see FIGS. 3, 3A, 4–8). Upper tray 16 has four corners or posts 16B that act to align filter plate FP with dispensing head plate 16A. Upper tray 16 also has a seal 16C to form an air tight union between filter tray FP and upper plate 16. As noted hereinbefore, upper tray 16 defines a collar along the bottom surface thereof to engage seal 18D around the top perimeter surface of lower tray 18 (see FIGS. 3, 3A and 5). Also, the collar of upper tray 16 acts to encase a microplate carried by lower tray 18 when the lower tray is raised into the vacuum forming position with upper tray 16. As previously noted, posts 18B are provided at the corners of lower tray 18 to facilitate aligning a conventional 96 well microplate therein with filter plate FP supported thereabove by upper tray 16. The bottom surface of lower tray 18 is tapered towards two apertures 18A to which vacuum lines 18C are attached to reduce the amount of fluid retained on the surface of lower tray 18 when a collection microplate is not utilized in the cell harvesting procedure. Applicants have also designed a custom accessory board circuit 28 (see FIGS. 9 and 10) to control the raising and lowering of lower tray 18.

Accessory board circuit 28 monitors the line on the SLT 96PW motherboard controller 24 that fires vacuum solenoid valve 26 so that when the line goes high, accessory board circuit 28 activates 4-way solenoid valve 30 to allow compressed gas to raise pneumatic cylinder 20. When the line on motherboard controller 24 goes low, accessory board circuit 28 delays for approximately 2 seconds and then switches 4-way solenoid valve 30 again to redirect the air flow through the 4-way solenoid valve so that lower tray 18 is vertically lowered. The 2 second delay allows time for enough air to pass through the bleed hole located on the front of upper tray 16 (not shown) to relieve the vacuum within the chamber formed by upper tray 16, lower tray 18, and filter plate FP (or optionally, upper plate 16, lower plate 18, filter plate FP and a microplate carried on lower plate 16).

Biological filter plates FP are frequently slightly bowed and they do not inherently seal well without some assistance. Applicants have addressed this issue by providing a mechanism for clamping filter plate FP to upper tray 16 with a clamp mechanism as best seen in FIGS. 3, 3A–4 and 5–8. Clamping mechanism 30 consists of a pivotably mounted upper linkage 32 provided at each end of upper tray 16 which is caused to pivot upwardly by pivot arm 34 pivotably mounted at one end to lower tray 18 and at the other end to upper linkage 32. Thus, when lower tray 18 is caused to move vertically upwardly, upper linkage 32 at each end of upper tray 16 pivots upwardly so as to cause fingers 32A to pivot into position against opposing ends of filter plate FP. Fingers 32A at each end of filter plate FP act to rotate into position against filter plate FP (between the two layers of filter plate FP) and to lightly press down on the bottom of filter plate FP to flatten the plate and form a satisfactory seal of filter plate FP against seal 16C of upper tray 16.

Pneumatic cylinder 20 that acts to vertically motivate lower tray 18 is energized from a pressurized gas source (not shown) through a hole in the housing of apparatus 100. The gas most suitably passes through a pressure regulator and flow regulator (not shown) to limit the speed and force with which lower tray 18 is moved. The original vacuum line of the SLT 96PW has been re-routed by applicants from the back of dispensing head 12 to vacuum lines 18C of lower tray 18.

Method of Use

Apparatus 10 for automated biological cell harvesting is used in somewhat the same manner as the original SLT 96PW microplate washer from which it is derived. The electrical, fluid and vacuum lines are attached to apparatus 10 in much the same way as the original microplate washer apparatus. A pressurized gas source has been added, however, to drive pneumatic cylinder 20, and it is attached to the rear of apparatus 10 with a connector (not shown). Motherboard controller 24 has not been modified (other than tapped for an electrical connection to accessory board 28) and acts to control apparatus 10 with the same commands as it controlled the SLT 96PW microplate washer.

The primary difference occurs whenever a signal is sent to vacuum valve 26. When the original SLT 96PW apparatus is asked to "aspirate" or wash a microplate, the head is lowered to a predetermined height associated with a particular microplate type and vacuum to the head is actuated. As the stainless steel tubes lower into the solution within the wells, the liquid is drawn out by the aspiration tubes through the vacuum manifold and vacuum valve and out of the apparatus where it is collected in a trap on the vacuum line.

In contrast, when vacuum valve 26 of automated cell harvesting apparatus 10 is activated, dispensing head 12 is lowered as before. Simultaneously with the opening of vacuum valve 26, applicants' new accessory board circuit 28 acts to raise lower tray 18. As lower tray 18 rises, clamping mechanism 30 acts to pivot fingers 32A into position against filter plate FP. Once fingers 32A and lower tray 18 are in place, a chamber is created where a vacuum can form and air is removed from the chamber by repositioned vacuum lines 18C (see FIG. 7). As pressure is lowered in the chamber, the pressure differential forces the fluid in the 96 well filter plate above the chamber through the well filters, and the removed liquid can then proceed to exit the system and be collected as waste or (if a microplate is carried on lower tray 18) it can be collected in a 96 well microplate.

After a preset amount of time is passed, accessory board circuit 28 terminates the vacuum. Lower tray 18 is held in position for approximately 2 seconds to allow the chamber's pressure to equalize with the ambient pressure. The equalization occurs as air continues to pass through both the filters of filter plate FP and the small hole (not shown) on the front of the chamber defined in upper tray 16. The hole assures that the pressure will equalize even if filter plate FP filters are clogged or otherwise air impermeable. If the delay is not present, the low pressure over the relatively large area of the chamber will prevent small pneumatic cylinder 20 from pulling lower tray 18 down.

Thus, applicants' apparatus for automated cell harvesting maintains many of the features of the SLT 96PW microplate washer from which it is derived, but the modifications thereto surprisingly allow for extracting solids from liquids in filter plates. The liquid extracted from the wells of the filter plates can be collected either in mass or in the 96 distinct containers of a separate microplate. In this fashion novel apparatus 100 provides automated cell harvesting whereas previously the procedure was a tedious, multi-step semi-manual procedure.

It will be understood that various details of the invention may be changed without departing from the scope of the invention. Furthermore, the foregoing description is for the purpose of illustration only, and not for the purpose of limitation—the invention being defined by the claims.

What is claimed is:

1. An automated apparatus for harvesting materials from fluid carried by a filter plate, comprising:
   (a) a movable fluid dispensing head with a top and a bottom surface adapted to move from a first position to a second position and having a plurality of dispensing means on the bottom surface thereof;
   (b) a fixed upper tray positioned beneath and spaced apart from said fluid dispensing head and adapted to support a filter plate thereon comprising a plurality of fluid permeable wells therein corresponding to said dispensing head plurality of dispensing means, and said upper tray being fluid permeable to allow fluid from said filter plate to flow therethrough;
   (c) a movable lower tray positioned beneath said upper tray and adapted to move from a first spaced-apart and lowered position beneath said upper tray to a second raised position in engagement with said upper tray;
   (d) clamping means operatively connected to said upper tray for sealingly securing a filter plate thereto in response to said lower tray being raised to said second raised position in engagement with said upper tray;
   (e) first actuator means adapted to move said fluid dispensing head from said first position to said second position and back to said first position, and pump means to pump fluid through said fluid dispensing head when said fluid dispensing head is moved to its second position by said first actuator means;
   (f) second actuator means adapted to move said lower tray from said first lowered position to said second raised position and back to said first lowered position, and vacuum means to create a vacuum between said upper and lower trays when said lower tray is moved to its second raised position by said second actuator means so as to draw fluid from the plurality of wells of a filter plate supported on said upper tray into said lower tray to isolate material within said wells of said filter plate; and
   (g) controller means for selectively activating said first and second actuator means and said pump means and said vacuum means according to a predetermined time sequence.

2. An apparatus according to claim 1 wherein said clamping means is pivotably connected to said upper tray and operatively connected to said lower tray and comprises one or more fingers for applying pressure to a filter plate to sealingly secure the filter plate in position on said upper tray.

3. An apparatus according to claim 1 wherein said dispensing means is formed to provide one or more spray streams.

4. An apparatus according to claim 3 wherein said one or more spray streams comprises a plurality of spray streams directed outwardly from each other.

5. An apparatus according to claim 1 wherein said upper tray comprises a bottom support surface defining a plurality of apertures therein corresponding to the plurality of wells in a filter plate supported by said upper tray.

6. An apparatus according to claim 1 wherein said upper tray defines an opening in the bottom thereof extending beneath the plurality of wells in a filter plate supported on said upper tray.

7. An apparatus according to claim 1 wherein said lower tray comprises at least one aperture in the bottom thereof for applying a vacuum to said upper tray when raised to said second raised position.

8. An apparatus according to claim 7 wherein said lower tray is adapted to optionally carry a microplate thereon which defines a plurality of wells therein corresponding to said plurality of fluid permeable wells in said filter plate so that fluid drawn from said filter plate wells will be received in said corresponding plurality of microplate wells.

9. An apparatus according to claim 1 wherein said first actuator means is an electric motor and said pump means is an electric liquid pump.

10. An apparatus according to claim 1 wherein said second actuator means is a pneumatic cylinder and said vacuum means is a vacuum pump in operative connection with a vacuum valve.

11. An apparatus according to claim 1 wherein said controller means is a microprocessor circuit for automatically activating said first actuator means and pump means, and said second actuator and said vacuum means according to a predetermined timing sequence.

12. An apparatus according to claim 11 wherein said controller means is adapted to provide for selective manual control of the automated apparatus for selectively changing the timing sequence for cell harvesting or for other use applications.

13. An automated apparatus for harvesting biological cells from fluid carried by a biological filter plate, comprising:

(a) a vertically movable fluid dispensing head with a top and a bottom surface and adapted to move from a first raised position to a second lowered dispensing position and having a plurality of spray nozzles on the bottom surface thereof wherein each spray nozzle is formed to provide a pair of spray streams directed outwardly from each other and each of said pair of spray streams defines a 45° angle with the bottom surface of said fluid dispensing head;

(b) a fixed upper tray positioned beneath and spaced apart from said fluid dispensing head and adapted to support a biological filter plate thereon of the type defining a plurality of fluid permeable wells therein corresponding to said dispensing head plurality of spray nozzles, and said upper tray being fluid permeable to allow fluid from said biological filter plate to flow therethrough;

(c) a vertically movable lower tray positioned beneath said upper tray and adapted to move from a first spaced-apart and lowered position beneath said upper tray to a second raised position in engagement with said upper tray;

(d) first actuator means adapted to move said fluid dispensing head from said first raised position to said second lowered position and back to said first raised position, and pump means to pump fluid through said fluid dispensing head when said fluid dispensing head is moved to its second lowered position by said first actuator means;

(e) second actuator means adapted to move said lower tray from said first lowered position to said second raised position and back to said first lowered position, and vacuum means to create a vacuum between said upper and lower trays when said lower tray is moved to its second raised position by said second actuator means so as to draw fluid from the plurality of wells of a biological filter plate supported on said upper tray into said lower tray to isolate biological cells within said wells of said biological filter plate;

(f) clamping means operatively connected to said upper tray for sealingly securing a biological filter plate thereto in response to said lower tray being raised into engagement with said upper tray; and (g) a microprocessor for selectively activating said first and second actuator means and said pump means and vacuum means according to a predetermined time sequence.

14. An apparatus according to claim 13 wherein said plurality of spray nozzles comprise 96 spray nozzles.

15. An apparatus according to claim 13 wherein said upper tray comprises a bottom support surface defining a plurality of apertures therein corresponding to the plurality of wells in a biological filter plate supported by said upper tray.

16. An apparatus according to claim 13 wherein said upper tray defines an opening in the bottom thereof extending beneath the plurality of wells in a biological filter plate supported on said upper tray.

17. An apparatus according to claim 13 wherein said lower tray defines at least one aperture in the bottom thereof for applying a vacuum to said upper tray when raised to said second raised position.

18. An apparatus according to claim 17 wherein said lower tray is adapted to optionally carry a microplate thereon which defines a plurality of wells therein corresponding to said plurality of fluid permeable wells in said filter plate so that fluid drawn from said filter plate wells will be received in said corresponding plurality of microplate wells.

19. An apparatus according to claim 13 wherein said first actuator means is an electric motor and said pump means is an electric liquid pump.

20. An apparatus according to claim 13 wherein said second actuator means is a pneumatic cylinder and said vacuum means is a vacuum pump in operative connection with a vacuum valve.

21. An apparatus according to claim 13 wherein said microprocessor is adapted to provide for selective manual control of the automated apparatus for selectively changing the timing sequence for all harvesting or for other use applications.

* * * * *